United States Patent
Kremers et al.

(10) Patent No.: US 6,974,888 B2
(45) Date of Patent: Dec. 13, 2005

(54) PROCESS FOR PREPARING ORGANIC HYDROPEROXIDE CONTAINING PRODUCT

(75) Inventors: Antoon Paul Michael Kremers, Amsterdam (NL); Eduardus Petrus Simon Schouten, Amsterdam (NL); Cornelis Willem Adriaan Schram, Amsterdam (NL)

(73) Assignee: Shell Oil Company, Houston, TX (US)

( * ) Notice: Subject to any disclaimer, the term of this patent is extended or adjusted under 35 U.S.C. 154(b) by 38 days.

(21) Appl. No.: 10/757,657

(22) Filed: Jan. 14, 2004

(65) Prior Publication Data

US 2004/0147768 A1 Jul. 29, 2004

Related U.S. Application Data

(62) Division of application No. 10/359,952, filed on Feb. 6, 2003, now Pat. No. 6,700,005.

(30) Foreign Application Priority Data

Feb. 6, 2002 (EP) ................................. 02250791

(51) Int. Cl.$^7$ ........................ C07C 15/44; C07C 5/327; C07C 5/333
(52) U.S. Cl. ...................... 585/435; 549/529; 549/530; 568/815
(58) Field of Search ..................... 585/435; 568/815; 549/529, 530

(56) References Cited

U.S. PATENT DOCUMENTS 6,700,024 B2 * 3/2004 Du Cauze de Nazelle et al. .......................... 568/571

FOREIGN PATENT DOCUMENTS

JP 06-271317 * 4/1994

* cited by examiner

*Primary Examiner*—Ba K. Trinh

(57) ABSTRACT

Process for preparing alkylaryl hydroperoxide containing product, which process comprises:
(a) oxidation of an alkylaryl compound to obtain reaction product containing alkylaryl hydroperoxide,
(b) contacting with water at least part of the alkylaryl hydroperoxide containing reaction product obtained in step (a) which reaction product contains less than 0.05 % wt of sodium,
(c) separating the product of step (b) into a hydrocarbonaceous phase containing alkylaryl hydroperoxide and an aqueous phase,
(d) optionally repeating process steps (b) and (c) one or more times,
(e) contacting at least part of the hydrocarbonaceous phase containing alkylaryl hydroperoxide obtained in step (c) or (d) with olefin and catalyst to obtain alkylaryl hydroxide and oxirane compound, and
(f) separating at least part of the oxirane compound from the alkylaryl hydroxide.

4 Claims, No Drawings

US 6,974,888 B2

PROCESS FOR PREPARING ORGANIC HYDROPEROXIDE CONTAINING PRODUCT

This is a division of application Ser. No. 10/359,952 filed Feb. 6, 2003, now U.S. Pat. No. 6,700,005 the entire disclosure of which is hereby incorporated by reference The present invention relates to a process for preparing alkylaryl hydroperoxide containing product. Such product is suitable for use in various processes, such as in the preparation of oxirane compounds and in the preparation of alkenyl aryl.

BACKGROUND OF THE INVENTION

Processes for preparing propylene oxide employing alkylaryl hydroperoxide compounds, are well known in the art. As described in U.S. Pat. No. 5,883,268, such processes conventionally comprise peroxidation of ethylbenzene, followed by contacting the peroxidation reaction product with aqueous base in amount sufficient to neutralize acidic components thereof and separating the resulting mixture into an aqueous stream and a deacidified organic stream. The base contaminated, deacidified hydroperoxide stream is washed with water and the resulting mixture separated into an organics contaminated water phase and an organic phase having a reduced alkali metal content.

It has now been found that the peroxidation reaction product does not need to be washed with aqueous base. Surprisingly, the peroxidation reaction product can be washed with water only. An important advantage of the absence of a wash with aqueous base is that a larger amount of aqueous phase is allowable in the organic phase. The larger amount of aqueous phase is acceptable in the process according to the present invention as such aqueous phase will not contain aqueous base residue such as sodium salts. The presence of such compounds generally causes the problems in subsequent process steps. Water does not need to be rigorously removed in the process of the present invention and this makes that the separation of water and organic phase can be carried out in a more simple way. Furthermore, upsets in the plant leading to less efficient water removal are more acceptable in the present invention than they are in a conventional process.

It was found that alkylaryl hydroperoxide containing reaction product which was washed with water only, gave similar catalyst deactivation in a subsequent reaction as product washed with both aqueous base and water, while a higher yield of alkylaryl hydrogen peroxide was observed when the reaction product had been washed with water only. The latter is attributed to reduced decomposition of alkylaryl hydrogen peroxide. Such decomposition is thought to be catalysed by the presence of aqueous base at basic conditions. The similar deactivation is very surprising as a water wash removes very little contaminants such as benzoic acid, which are known to be present in the crude reaction product. Furthermore, less emulsion was observed to be formed when the alkylaryl hydroperoxide containing product was washed with water only.

WO 00/12470 describes a process for purifying a cyclohexyl hydroperoxide containing reaction mixture in order to make it suitable for decomposition or hydrogenation into cyclohexanol and cyclohexanone. This document contains no information on purification of an akylaryl hydroperoxide containing reaction mixture to be reacted with olefin in the presence of an epoxidation catalyst.

SUMMARY OF THE INVENTION

Surprisingly, a process has now been found which gives an improved alkylaryl hydroperoxide containing product.

The process for preparing organic hydroperoxide containing product according to the present invention comprises:

(a) oxidation of an alkylaryl compound to obtain reaction product containing organic hydroperoxide, (b) contacting with water at least part of the alkylaryl hydroperoxide reaction product obtained in step (a) which reaction product contains less than 0.05% wt of sodium, (c) separating the product of step (b) into a hydrocarbonaceous phase containing the alkylaryl hydroperoxide and an aqueous phase, (d) optionally repeating process steps (b) and (c) one or more times, (e) contacting at least part of the hydrocarbonaceous phase containing alkylaryl hydroperoxide obtained in step (c) or (d) with olefin and catalyst to obtain alkylaryl hydroxide and oxirane compounds, and (f) separating at least part of the oxirane compound from the alkylaryl hydroxide.

The product subjected to step (b) is considered to be the product in total. If any aqueous phase is present in the reaction product to be subjected to the water wash, the sodium content of this aqueous phase is taken into account as well. A conventional alkylaryl hydroperoxide containing product which has been neutralised with aqueous base, will generally contain of from 0.10 to 0.15% wt of sodium, based on total amount of both organic and aqueous phase, before it is subjected to a water wash.

It is preferred that water is removed from the hydrocarbonaceous phase containing alkylaryl hydroperoxide obtained in step (c) or (d) before this hydrocarbonaceous phase is subjected to step (e). A convenient and preferred method for removing water from this hydrocarbonaceous phase is distillation.

The alkylaryl hydroxide obtained in step (f) can be used in a wide range of processes. Such process is preparing an alkenyl aryl by dehydrating the alkylaryl hydroxide. Another process is hydrogenating the alkylaryl hydroxide to obtain an alkyl aryl. Therefore, the process according to the present invention suitably comprises further:

(g) converting at least part of the alkylaryl hydroxide obtained in step (f). Generally, the conversion produces reaction product and water.

Preferably, step (g) comprises either dehydration or hydrogenolysis of the reaction product. Hydrogenolysis is the reaction of the alkylaryl hydroxide with hydrogen, preferably in the presence of catalyst. Dehydration will generally produce an alkenyl aryl and water, while hydrogenolysis will generally produce alkylaryl. Preferably, the hydrogenolysis will produce the alkylaryl used as starting compound.

DETAILED DESCRIPTION OF THE INVENTION

Alkylaryl compounds which are most preferably used in the process of the present invention are benzene compounds containing at least 1 alkyl substituent which alkyl substituent contains of from 1 to 10 carbon atoms, preferably of from 2 to 8 carbon atoms. Preferably, the benzene compound contains-on average of from 1 to 2 constituents. The alkylaryl compounds most frequently encountered are ethylbenzene, cumene and di(iso-propyl) benzene.

The oxidation of the alkylaryl compound can be carried out by any suitable process known in the art. The oxidation can be carried out in the liquid phase in the presence of a diluent. This diluent is preferably a compound which is liquid under the reaction conditions and does not react with the starting materials and product obtained. However, the diluent can also be a compound necessarily present during the reaction. For example, if the alkylaryl is ethylbenzene the diluent can be ethylbenzene as well and if the alkylaryl is cumene the diluent can be cumene as well.

Besides the desired alkylaryl hydroperoxide, a range of contaminants are created during the oxidation of organic compounds. Although most of these are present in small amounts, it has been found that the presence of compounds such as organic acids can cause problems in further use of the alkylaryl hydroperoxides. As described in U.S. Pat. No. 5,883,268, the conventional method of reducing the amount of contaminants is by contacting the reaction product containing alkylaryl hydroperoxide with an aqueous alkali solution. However, contact with the aqueous alkali solution introduces alkali metal into the hydroperoxide containing reaction product. Although the amount of organic acids present in the hydroperoxide containing product can be decreased by the alkali wash, the amount of alkali metal contaminants is increased.

It has now been found that a simple water wash is more efficient in purifying reaction product containing hydroperoxide than a treatment with aqueous base followed by a water wash. According to the present invention, the hydroperoxide containing product preferably is not contacted with aqueous base, more specifically sodium hydroxide, between the time at which it is produced by oxidation of organic compound and the time at which it is reacted further.

Aqueous base most often used in conventional processes, are sodium and/or potassium containing bases such as sodium hydroxide, potassium hydroxide, sodium carbonate and potassium carbonate. Decomposition of hydroperoxide is thought to be catalysed by the presence of these salts at basic conditions. Therefore, it is preferred that the product sent to step (b) contains less than 0.010% wt of sodium, preferably less than 0.005% wt of sodium, more preferably less than 0.002% wt of sodium, most preferably less than 0.001% wt of sodium. The amount of sodium is the weight amount of metallic or ionic sodium on total amount of product, including both the organic phase and any aqueous phase which might be present. Furthermore it is preferred that the product sent to step (b) contains less than 0.050% wt of potassium, preferably less than 0.010% wt of potassium, most preferably less than 0.002% wt of potassium. The amount of potassium is the weight amount of metallic or ionic potassium on total amount of product, including both the organic phase and any aqueous phase which might be present.

The reaction product of step (a) can be sent to step (b) as such. However, it is preferred to remove light compounds from the reaction product obtained. These light products can be removed by subjecting the reaction product of step (a) to distillation, preferably distillation at reduced pressure. A distillation which is especially suitable is so-called flash distillation, which comprises distillation at very low pressure. It has been found that such flash distillation is efficient in removing light compounds such as oxygen and light acids formed during the oxidation.

In the process according to the present invention, the reaction product of step (a) is contacted with water. The water which can be used can contain contaminants, such as organic compounds. Such contaminants can have been introduced by the recycle of at least part of the wash water, either to the same wash step or to another wash step. The water can be fresh water only, it can be a combination of fresh water containing substantially no contaminants and one or more different waste water streams, or it can consist only of different kinds of waste water streams or it can consist of a single type of waste water.

The speed by which the equilibrium is reached in which contaminants are removed as far as possible, can be increased in the ways known to someone skilled in the art. The contact between the reaction product containing alkylaryl hydroperoxide and water can be improved by intense contact of the hydroperoxide containing reaction product and water. Such intense contact can be achieved in any way known in the art, for example by intense mixing. However, a conventional water wash will suffice for most processes according to the present invention.

The exact conditions under which the water wash is carried out, strongly depend on further circumstances. Preferably, the water wash is carried out at a temperature of between 0° C. and 150° C., more preferably of between 20° C. and 100° C.

In step (c), the product of step (b) is separated into a hydrocarbonaceous phase and an aqueous phase. A preferred method comprises allowing the hydrocarbonaceous phase and aqueous phase to settle in a settling vessel and subsequently separating a hydrocarbonaceous phase from an aqueous phase. The hydrocarbonaceous phase containing alkylaryl hydroperoxide can subsequently be sent to a coalescer where further aqueous phase is removed. Preferably, step (c) is carried out at a temperature of between 0° C. and 150° C., more preferably of between 20° C. and 100° C.

Further water, unconverted organic compounds and contaminants can be separated by distillation from the hydrocarbonaceous phase obtained from the coalescer. Generally, the distillate contains unconverted organic compounds, water and contaminants. The distillate obtained can subsequently be phase separated in a vessel to obtain an organic phase and an aqueous phase. The aqueous phase obtained in this way, will contain organic contaminants and can be used as water for washing alkylaryl hydroperoxide containing reaction product.

Water which can be used in the present invention is water previously used in washing a hydrocarbonaceous phase containing alkylaryl hydroperoxide. Preferably, such water is obtained by contacting a hydrocarbonaceous phase containing alkylaryl hydroperoxide with an aqueous phase, preferably clean water, and subsequently separating the aqueous phase from the hydrocarbonaceous phase. The aqueous phase so obtained can be used without further treatment.

As mentioned above, a very thorough separation of aqueous phase and hydrocarbonaceous phase is generally not necessary in the process of the present invention. Therefore, steps (b) and (c) preferably consist of contacting the reaction product containing organic hydroperoxide obtained in step (a) with water in an extraction column. More preferably, the extraction column is operated in counter current mode.

Waste water streams which might be used as part or total of the water in step (b) of the present process, are prepared in several ways in the process according to the present invention. Preferred waste water streams for use as water for use in the present invention contain at least part of one or more of the following waste water streams: waste water produced as by-product in the oxidation of alkylaryl compound in step (a), waste water obtained in cleaning filters for off-gas, aqueous distillate obtained by distillation of hydrocarbonaceous phase obtained in step (c) and water obtained in converting alkylaryl hydroxide in step (g). These streams are being discussed in more detail herein below.

In the oxidation of the alkylaryl compound, it has been observed that water can be produced. It is thought that this water originates from side-reactions such as the decomposition of hydroperoxide. A waste water stream which can be used in step (b) can be recovered by condensation of the reactor offgas, and separating the hydrocarbonaceous phase.

In the oxidation of the organic compound, off-gas is produced containing organic contaminants. One of the possibilities to clean this off-gas, is with the help of a filter, more specifically a charcoal filter. The filter has to be cleaned regularly to remove the absorbed contaminants. Usually, this is done with the help of water optionally containing small amounts of further compounds. It has been found that such waste water obtained in cleaning filters for off-gas is especially suitable for use as water in step (b).

Another waste water stream which has been found suitable for use as water for step (b), is aqueous distillate obtained by separating hydrocarbonaceous phase from aqueous phase, distilling the hydrocarbonaceous phase and subsequently separating the hydrocarbonaceous distillate from the aqueous distillate. Preferred embodiments for preparing such aqueous distillate for use as waste water in step (b) have been described above in the discussion of step (b). Such aqueous distillate is especially suitable for use as water in step (b). Generally, the conversion process produces reaction product and water.

A further stream which is especially suitable for use as water is the water obtained in the conversion of alkylaryl hydroxide of step (g). As mentioned above, the conversion preferably is dehydration or hydrogenolysis. If step (g) comprises dehydration, the product of the dehydration is preferably distilled whereby the distillate obtained contains water and organic compounds. This distillate is phase separated by separating off hydrocarbonaceous phase in a settler and sending the aqueous phase to a coalescer. The aqueous phase obtained in the coalescer can very suitably be used as waste water in step (b). If step (g) comprises hydrogenolysis, the water produced can be used as water in step (b), preferably after the hydrocarbonaceous phase has been separated off by phase separation. If the hydrogenolysis gives the alkylaryl compound used as starting product, the alkylaryl compound obtained in step (g) is suitably recycled to step (a).

In process step (e), at least part of the hydrocarbonaceous phase containing alkylaryl hydroperoxide obtained in step (d) is contacted with olefin, preferably propene, in the presence of a catalyst to obtain alkylaryl hydroxide and oxirane compounds. A catalyst which can suitably used in such process comprises titanium on silica and/or silicate. A preferred catalyst is described in EP-A-345856. The reaction generally proceeds at moderate temperatures and pressures, in particular at temperatures in the range of from 0 to 200° C., preferably in the range from 25 to 200° C. The precise pressure is not critical as long as it suffices to maintain the reaction mixture as a liquid or as a mixture of vapour and liquid. Atmospheric pressure may be satisfactory. In general, pressures can be in the range of from 1 to $100 \times 105$ N/m$^2$.

The reaction product of step (c) or (d) is preferably subjected to distillation before being used in step (e). The distillation removes light products such as water which can be harmful to a subsequent catalyst.

The oxirane compounds can be separated from the reaction product containing alkyl aryl hydroxide in any way known to be suitable to someone skilled in the art. The liquid reaction product may be worked up by fractional distillation, selective extraction and/or filtration. The solvent, the catalyst and any unreacted olefin or alkylaryl hydroperoxide may be recycled for further utilization.

The alkylaryl hydroxide obtained in the process can be dehydrated in the presence of a catalyst to obtain styrene and water. Processes which can be used for this step have been described in WO 99/42425 and WO 99/42426. However, any suitable process known to someone skilled in the art can in principle be used.

The present invention is further illustrated by the following examples.

EXAMPLE 1

In a reactor, air was blown through ethylbenzene. The product obtained contained ethylbenzene hydroperoxide.

To 200 grams of this product of room temperature was added 800 grams of demineralized water, and the combination was mixed for 1 hour. Subsequently, the mixture was allowed to settle overnight and was phase separated. The organic phase obtained was distilled at 30 mbar and 50–55° C. The product obtained is called "water washed feed".

COMPARATIVE EXAMPLE 1

Another part of the product containing ethylbenzene hydroperoxide prepared in Example 1, was contacted with a solution containing 0.5% wt NaOH in water and mixed at a temperature of 60° C. The weight ratio of product containing ethylbenzene hydroperoxide to NaOH containing solution was 4.5:1 (wt:wt). The neutralized mixture obtained was allowed to settle and was subsequently phase separated into a neutralized hydrocarbonaceous phase containing ethylbenzene hydroperoxide and an aqueous phase. The neutralized hydrocarbonaceous phase containing ethylbenzene hydroperoxide was subsequently washed twice with water. The product obtained is called "neutralised and washed feed".

COMPARATIVE EXAMPLE 2

A further part of the product containing ethylbenzene hydroperoxide prepared in Example 1, was distilled at 30 mbar and 50–55° C. The product obtained is called "non-washed feed".

EXAMPLE 2

Each of the above feeds prepared in Example 1, Comparative example 1 and Comparative example 2 contained 35% wt of ethylbenzene hydroperoxide, and were tested in the following way. A feed solution was prepared by mixing 340 g 1-octene, 200 g of ethyl benzene hydroperoxide solution in ethylbenzene and 400 g of ethyl benzene. The ethyl benzene hydroperoxide concentration was determined by titration of an aliquot of the feed. A 100 ml round bottom flask equipped with a condensor and a stirrer bar was charged with 50 ml of the feed solution and 1.00 g of catalyst. The catalyst contains titanium on silica and was prepared as described in the Example according to the teaching of EP-A-345856. The flask was immersed in a 40° C. oil bath while the contents was stirred. After 1 hour, the ethyl benzene hydroperoxide concentration was determined by titration of an aliquot of the reaction mixture. The ethylbenzene hydroperoxide conversion was calculated as the amount of ethylbenzene hydroperoxide converted divided by the amount of ethylbenzene hydroperoxide converted when using the neutralised and washed feed. The results obtained are given in Table 1.

TABLE 1

|  | ethylbenzene hydroperoxide conversion (relative) |
|---|---|
| non-washed feed | 0.81 |
| water washed feed | 0.97 |
| neutralised and washed feed | 1.00 (by definition) |

COMPARATIVE EXAMPLE 3

This experiment was carried out in a 1 liter jacketed reactor equipped with a turbine stirrer, temperature control device and heating oil batch system. The reactor was charged with 561.2 g. of a solution containing 26.34% wt of ethylbenzene hydroperoxide in ethylbenzene. This solution was heated to 70° C. After the extraction temperature was reached about 300 ml of a caustic solution was added in one shot. The caustic solution consisted of demineralised water containing 6.8% wt sodium benzoate and 0.4% wt sodium hydroxide. The caustic solution was preheated to the same temperature in a separate vessel before being added to the organic phase.

After mixing for 15 minutes, the organic phase was separated and analysed for ethylbenzene hydroperoxide content by iodometric titration. The ethylbenzene hydroperoxide content was found to be 25.72% wt.

EXAMPLE 3

The experiment of Comparative example 3 was repeated differing only in that this time the organic phase was mixed with demineralised water only.

After mixing for 15 minutes, the organic phase was separated and analysed for ethylbenzene hydroperoxide content by iodometric titration. The ethylbenzene hydroperoxide content was found to be 26.07% wt.

What is claimed is:

1. A process for preparing an alkenyl aryl, which process comprises:
    preparing an alkylaryl hydroxide containing product, by a process comprising:
        (a) oxidating an alkylaryl compound to obtain reaction product containing alkylaryl hydroperoxide;
        (b) contacting with water at least part of the alkylaryl hydroperoxide containing reaction product obtained in step (a) which reaction product contains less than 0.05% wt of sodium;
        (c) separating the product of step (b) into a hydrocarbonaceous phase containing alkylaryl hydroperoxide and an aqueous phase;
        (d) optionally repeating process steps (b) and (c) one or more times;
        (e) contacting at least part of the hydrocarbonaceous phase containing alkylaryl hydroperoxide obtained in step (c) or (d) with olefin and catalyst to obtain alkylaryl hydroxide and oxirane compound;
        (f) separating at least part of the oxirane compound from the alkylaryl hydroxide; and,
    dehydrating at least part of the alkylaryl hydroxide obtained in step (f) to an alkenyl aryl.

2. The process of claim 1 which process further comprises distilling the product obtained in step (c) or (d), and sending to step (e) hydrocarbonaceous phase from which light compounds have been distilled off.

3. The process of claim 2 in which process steps (b) and (c) are carried out in an extraction column.

4. The process of claim 3 in which process the product sent to step (b) further contains less than 0.05 wt % of potassium.

* * * * *